(12) United States Patent
Tallman et al.

(10) Patent No.: US 6,737,242 B1
(45) Date of Patent: May 18, 2004

(54) METHODS FOR SCREENING GABA-MODULATORY COMPOUNDS FOR SPECIFIED PHARMACOLOGICAL ACTIVITIES

(75) Inventors: John Tallman, New York, NY (US); Dorothy Gallager, Columbus, MT (US); Kenneth Shaw, Weston, CT (US); Geoffrey White, Guilford, CT (US); Marci Crandall, Middletown, CT (US); James Cassella, Guilford, CT (US); Lavanya Rajachandran, Wallingford, CT (US); Pamela Albaugh, Clinton, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/565,524

(22) Filed: May 5, 2000

Related U.S. Application Data

(60) Provisional application No. 60/133,195, filed on May 7, 1999, provisional application No. 60/133,191, filed on May 7, 1999, provisional application No. 60/133,155, filed on May 7, 1999, and provisional application No. 60/133,154, filed on May 7, 1999.

(51) Int. Cl.$^7$ ............................................. G01N 33/567
(52) U.S. Cl. ....................... 435/7.21; 435/7.1; 435/69.1; 435/252.3; 435/320.1; 436/501; 530/350; 536/23.5
(58) Field of Search ................................. 435/7.1, 7.21, 435/69.1, 252.3, 320.1; 436/501; 530/350; 536/23.5

(56) References Cited

FOREIGN PATENT DOCUMENTS

| | | |
|---|---|---|
| WO | WO 93/22681 | 11/1993 |
| WO | WO 96/25948 | 8/1996 |
| WO | WO98/19165 | * 5/1998 |

OTHER PUBLICATIONS

Steadman's Medical Dictionary, 27th Edition, Lippincott Williams & Wilkins, 2000.*
Rudolph et al., Nature 401(796–799)1999.*
Mohler, H. et al., "Heterogeneity of GABA$_A$–Receptors: Cell–Specific Expression, Pharmacology, and Regulation", *Neurochemical Research*, vol. 20, No. 5, 1995, pp. 631–636.
Lüddens, Hartmut et al., "Biological Function of GABA$_A$/Benzodiazepine Receptor Heterogeneity", *J. psychiat. Res.* vol. 29, No. 2, 1995, pp. 77–94.
Atack, Hohn R. et al., "Regional Differences in the Inhibition of Mouse In Vivo[$^3$H]Ro 15–1788 Binding Reflect Selectivity for $\alpha_2$ and $\alpha_3$ Subunit–Containing GABA$_A$ Receptors", *Neuropsychopharmacology*, vol. 20, No. 3, 1999, pp. 255–262.
Cost, Erminio et al., "Benzodiazepines on trial: a research strategy for their rehabilitation", *TiPS*, vol. 17, May 1996, pp. 192–200.

* cited by examiner

*Primary Examiner*—Yvonne Eyler
*Assistant Examiner*—Michael Brannock
(74) *Attorney, Agent, or Firm*—McDonnell Boehnen Hulbert & Berghoff LLP

(57) ABSTRACT

Methods are provided that are useful in assaying compounds for cognitive enhancing properties, anxiolytic properties, hypnotic properties, or antidepressant properties. These methods involve determining the in vitro efficacy and EC$_{50}$ of the compounds at defined series of cloned GABA$_A$ subtype receptors composed of specific variants of $\alpha, \beta,$ and $\gamma$ subunits in order to develop and an activity profile for each compound. Optionally, the binding affinities of the compounds at GABA$_A$ receptors are also determined. As an additional step the in vivo effects of the compounds may be tested in animal models.

12 Claims, No Drawings

METHODS FOR SCREENING GABA-MODULATORY COMPOUNDS FOR SPECIFIED PHARMACOLOGICAL ACTIVITIES

CROSS REFERENCE TO RELATED APPLICATIONS

This application claims priority from U.S. provisional applications 60/133,195, entitled "Methods for Screening Compounds for Cognition Enhancing Activity", No. 60/133.191, entitled "Methods for Screening Compounds for Antidepressant Activity", No. 60/133,155, entitled "Methods for Screening Compounds for Hypnotic Activity", and No. 60/133,154, entitled "Methods for Screening Compounds for Anxiolytic Activity", each of which was filed in the names of the present inventors on May 7, 1999. To the extent that they differ from the disclosure of the present application, the disclosures (including the claims) of these provisional applications are incorporated herein by reference.

BACKGROUND OF THE INVENTION

1. Field of the Invention

The present invention relates to methods for assaying GABA-modulatory compounds for activity as antidepressants, cognitive enhancers, sedative hypnotics, or non-sedating anxiolytics. In particular, the method includes determining efficacy (generally in vitro efficacy) and $EC_{50}$ values (as used herein incorporating $IC_{50}$ values) for the compounds at several different cloned (i.e., expressed in cells as directed by heterologous cloned receptor-encoding nucleic acid expression vector molecules) $GABA_A$ subtype receptors (each subtype made up of a defined set of specific receptor subunit isotypes). The method optionally includes determining binding affinity of compounds for $GABA_A$ receptors. The method results in the development of an activity profile for each compound. As an additional step, animal models predictive of such effects may be used to measure the ability of compounds to effect cognitive enhancement, to act as antidepressants, to mediate sedative hypnotic effects, or to effect anxiolysis in vivo without eliciting certain undesirable side effects.

2. Description of Related Art

Modern drug discovery methodology allows the testing of large numbers of compounds (often assembled into collections termed libraries) for functional characteristics that confer pharmaceutical utility. This "screening" of such libraries, using specific tests (assays) for functional activity properties, allows the rapid identification of promising compounds for further development as pharmaceutical agents. There has been a longstanding quest in the pharmaceutical industry for new means of identifying such promising compounds. Such new means may involve new assays, or may use old assays to generate data that can be analyzed and applied in new ways to identify compounds with new and useful characteristics.

In the field of psychopharmacology, the use of cloned neuronal receptors as substrates has, provided new, more specific assays with which compounds can be characterized. The use of such receptors has enabled the development of receptor binding profile criteria that are particularly beneficial in the identification of useful psychopharmacological agents. For example, such profiling can identify compounds that will be free of certain undesirable adverse effects (side effects).

The $GABA_A$ receptor superfamily represents one of the classes of receptors through which the major inhibitory neurotransmitter, γ-aminobutyric acid, or GABA acts. In addition to being the site of neurotransmitter action a number of drugs including the anxiolytic and sedating benzodiazepines bind to this receptor. The $GABA_A$ receptor is a chloride channel that opens in response to GABA, allowing chloride to enter the cell. This effects a slowing of neuronal activity through hyperpolarization of the cell membrane potential. $GABA_A$ receptors are composed of several protein subunits and are generally pentameric in structure.

A number of cDNAs for $GABA_A$ receptor subunits have been cloned. While these subunits share a basic motif of 4 membrane-spanning helices, there is sufficient sequence diversity to classify them into several groups. To date at least 6α, 3β, 3γ, 1ε, 1δ, 2ρ, and 1π subunit species have been identified; some representing alternatively spliced forms. Native $GABA_A$ receptors are typically composed of α, β, and γ subunits, most often in the ratio of two alphas, two betas, and one gamma, although other combinations (some comprising other subunits such as ε, δ, ρ, or π) have been described. Even if restricted to only α, β, and γ subunits, however, an enormous diversity of $GABA_A$ subtype receptors are possible. Evidence such as message distribution, genome localization and biochemical studies suggests that the major naturally occurring receptor combinations are $α_1β_2γ_2$, $α_2β_3γ_2$, $α_3β_3γ_2$, and $α_5β_3γ_2$.

In the typical $GABA_A$ receptor, the binding sites for GABA (2 per receptor complex) are formed by amino acids from the α and β subunits. Amino acids from the α and γ subunits contribute to form 1 benzodiazepine site per receptor complex. In a classic allosteric mechanism, the binding of a drug to the benzodiazepine site increases the affinity of GABA binding to the receptor. Benzodiazepines and related drugs that enhance the ability of GABA to open $GABA_A$ receptor channels are known as agonists or partial agonists depending on the level of enhancement. Other classes of drugs such as β-carboline derivatives that occupy the same site and negatively modulate the action of GABA are called inverse agonists. A third class of compounds exists that occupies the same site as both the agonists and inverse agonists (blocking access of these agents to the site) and yet has little or no direct effect on GABA activity. These compounds are referred to as antagonists.

The characterization of activities of different subtype receptors has been an area of intense pharmacological discovery. Agonists that act at the benzodiazepine site have long been known to know to exhibit anxiolytic, sedative, and hypnotic effects in animal behavior models, while compounds that act as inverse agonists at this site elicit anxiogenic, cognition enhancing, and proconvulsant effects. While benzodiazepines have long been used as anxiolytics, these compounds exhibit a number of undesirable side effects. These include cognitive impairment, sedation, ataxia, potentiation of ethanol effects, and a tendency for tolerance and drug dependence. Likewise the development of benzodiazepine site ligands for other indications has been thwarted by unfavorable side effect profiles for each indication. For example, compounds known to possess cognition enhancing properties have generally tended to be anxiogenic and proconvulsant, while compounds that produce anxiolytic effects tend to generate unwanted sedation, and do so more powerfully when taken in conjunction with the consumption of alcoholic beverages.

SUMMARY OF THE INVENTION

The present invention provides methods for characterizing compounds that act at the $GABA_A$ receptor benzodiazepine site. In particular, it provides methods for identifying compounds with characteristics indicating that the identified compounds will exhibit pharmacological properties consistent with their use as antidepressants, cognitive enhancers without anxiogenic or proconvulsant activity, sedative hypnotics without cognition-impairing activity, or non-sedating anxiolytics.

This invention is useful in screening libraries of compounds for therapeutic potential and in drug design efforts.

Measurement of GABA receptor binding affinity is a useful step in any of the methods of the invention. Alternatively, these assays may be performed without measuring the binding affinity of the compound. The assays may include an assessment of the ability of the compound to mediate the desired effects in vivo without eliciting side effects using animal models established to be predictive of the desired effects and animal models predictive of the undesired side effects that have been associated with other compounds acting at $GABA_A$ receptors.

As used herein, the term "efficacy" refers to amount of potentiation (represented as a % increase, e.g., 10%) or inhibition (represented as a % decrease, e.g., -10%) of GABA activated responses measured for $GABA_A$ receptors.

In addition to the ability of a compound to effect a specified magnitude of change in the GABA response at distinct subtype receptors, the $EC_{50}$ value of the compound at the pertinent receptors is also taken into consideration. As used herein, the term "$EC_{50}$" or "$EC_{50}$ value" refers to the concentration of a compound needed to elicit half the maximal response (to the agonist or inverse agonist effects of a compound) that can be obtained with the compound. Thus, a compound that exhibits dissimilar $EC_{50}$ values at different subtype receptors can selectively potentiate one of those receptors over a defined range of drug concentrations, even though the maximal amount of potentiation achievable by the compound is the same for the two subtype receptors over a much broader range of compound concentrations. $EC_{50}$ values do not necessarily correlate to binding affinities or to compound efficacies.

Cognitive Enhancers: With regard to identifying cognitive enhancers, a method of the invention involves optionally determining the binding affinity of a compound for $GABA_A$ receptors having Ro15–1788 binding sites and determining efficacy and $EC_{50}$ values for the compound at cloned $\alpha_1\beta_2\gamma_2$ and $\alpha_5\beta_3\gamma_2$ receptors and comparing these values with efficacy and $EC_{50}$ values for the compound at cloned $GABA_A$ receptors containing the $\alpha_2$ or $\alpha_3$ subunits. The ability of the compound to mediate cognitive enhancing effects may optionally be assessed in vivo by animal model predictive of cognitive enhancement. Whether the compound causes proconvulsant effects may also be assessed in vivo using animal models for detecting proconvulsant activity.

Accordingly, in one aspect this invention provides methods for identifying compounds with cognitive enhancing activity that do not display the side effects of anxiogenesis or proconvulsant activity. These methods comprise:

a) Screening compounds, optionally determining the binding affinity of the compounds for $GABA_A$ receptors;

b) determining in vitro efficacy and $EC_{50}$ values of the compounds using cloned $\alpha_1\beta_2\gamma_2$ and $\alpha_5\beta_3\gamma_2$ receptors and comparing these values to in vitro efficacy and $EC_{50}$ values for the compound determined using $GABA_A$ receptors that contain the $\alpha_2$ or $\alpha_3$ subunit; and c) selecting compounds having significant inverse agonist character and sufficiently low $EC_{50}$ values at $\alpha_1\beta_2\gamma_2$ or $\alpha_5\beta_3\gamma_2$ subtype receptors and that produce agonist activity at $GABA_A$ subtype receptors that contain the $\alpha_2$ or $\alpha_3$ subunit.

Thus, the invention presents novel methods for identifying compounds with selective cognitive enhancing properties (1) by examining the binding of a given compound at $GABA_A$ receptors and (2) by assessing the ability of the compound to potentiate GABA responses at a series of $GABA_A$ subtype receptors. These values are then compared to a set of criteria termed the "Cognitive Enhancer Activity Range Profiler" (Table I, below). This activity profile comprises measurements of in vitro efficacy (agonist, inverse agonist or antagonist character) and $EC_{50}$ values at each of 4 $GABA_A$ subtype receptors. The activity profile needed for cognitive enhancement is presented as a precise window of inverse agonism at certain subtype receptors and agonism at other subtype receptors. The $EC_{50}$ criteria at each of these subtype receptors are also presented. Determining efficacy and $EC_{50}$ values for a test compound is crucial as many compounds bind with high affinity at the benzodiazepine site without potentiating the GABA response at the appropriate subtype receptors.

In certain embodiments, the conclusions drawn from the in vitro determinations of validity may be confirmed by examining the in vivo efficacy of test compounds as cognitive enhancers using animal models for cognitive enhancement.

It may also be necessary to verify that compounds identified by these methods possess the predicted favorable side effect profiles by examining the performance of the compounds in animal models indicative of these side effects. Thus, the animal models may be used as an additional step of the assay to further refine the selection of compounds with cognitive enhancing activity.

Anxiolytics: With regard to identifying anxiolytics, a method of the invention involves optionally measuring the binding affinity of a compound at $GABA_A$ receptors having Ro15–1788 binding sites and measuring the efficacy and $EC_{50}$ values for a compound using cloned $\alpha_2\beta_3\gamma_2$ and $\alpha_3\beta_3\gamma_2$ receptors and comparing these values with the activities and $EC_{50}$ values of the compound at cloned $GABA_A$ receptors containing the $\alpha_1$ or $\alpha_5$ subunits. As an additional step, the ability of the compound to mediate anxiolytic effects may be assessed in vivo using an animal model established to be predictive of anxiety, and whether the compound causes sedative effects may also be assessed in vivo by an animal model shown to measure sedation.

Accordingly, this invention provides a method for identifying compounds with anxiolytic activity that do not display the side effects of cognitive impairment, ataxia, potentiation of alcohol effects, and a tendency for tolerance and drug dependence or that display these side effects only to a very minimal degree. These method comprise:

a) screening compounds, optionally measuring the binding affinity of the compounds at $GABA_A$ receptors;

b) measuring the in vitro efficacy and $EC_{50}$ values of the compounds at cloned $\alpha_2\beta_3\gamma_2$ and $\alpha_3\beta_3\gamma_2$ receptors and comparing these values to the in vitro efficacy and $EC_{50}$ values of the compounds at $GABA_A$ receptors that contain the $\alpha_1$ or $\alpha_5$ subunit; and c) selecting compounds with partial agonist character and sufficiently low $EC_{50}$ values at $\alpha_2\beta_3\gamma_2$ and $\alpha_3\beta_3\gamma_2$ subtype receptors that also display lower activity at $GABA_A$ subtype receptors that contain the $\alpha_1$ or $\alpha_5$ subunit.

Alternatively, this assay may be performed without measuring the binding affinity of the compound or with the additional step of assessing the ability of the compound to mediate anxiolytic effects in vivo without causing sedation via an animal model established to be predictive of anxiety and an animal model predictive of sedative effects.

Thus, the invention presents a method for identifying compounds with selective anxiolytic activity (1) by examining the binding of a given compound at GABA$_A$ receptors and (2) by assessing the ability of the compound to potentiate GABA responses at a series of GABA$_A$ subtype receptors. The resulting values are then compared to a set of empirically defined criteria termed the "Anxiolytic Activity Range Profiler" (Table III, below) The criteria given by the Anxiolytic Activity Range Profiler are used to select compounds with anxiolytic activity that have no or very minimal sedative effects. This activity profile comprises determinations of in vitro efficacy (agonist, inverse agonist or antagonist character) and EC$_{50}$ values at each of 4 GABA$_A$ subtype receptors. The activity profile needed for anxiolysis is presented as a precise window of agonism and EC$_{50}$ criteria at each of these subtype receptors. The combination of determining efficacy, and EC$_{50}$ values for a test compound is crucial as many compounds bind with high affinity at the benzodiazepine site without potentiating the GABA response at the appropriate subtype receptors.

In certain embodiments, the conclusions drawn from the in vitro determinations may be confirmed by examining the in vivo efficacy of test compounds predicted to have anxiolytic activity in an animal model for anxiety. It may also be desirable to verify that compounds identified by these methods possess the predicted favorable side effect profiles by examining the performance of the compounds in animal models known to be indicative of sedative effects. Thus, the animal models may be used as an additional step of the assay to further refine the selection of compounds with non-sedating anxiolytic properties.

Antidepressants: With regard to identifying antidepressants, a method of the invention involves optionally measuring the binding affinity of a compound at GABA$_A$ receptors, measuring the efficacy and EC$_{50}$ values for a compound at cloned $\alpha_2\beta_3\gamma_2$ and $\alpha_3\beta_3\gamma_2$ receptors, and comparing these values with efficacy and EC$_{50}$ values for the compound at cloned GABA$_A$ receptors containing the $\alpha_1$ or $\alpha_5$ subunits. Optionally, the ability of the compound to mediate antidepressant effects may be assessed in vivo using one or more animal models predictive of antidepressant activity. Whether a compound produces sedative effects may also be assessed in vivo with an animal model for measuring sedation.

Accordingly in a broad aspect, this invention provides a method for screening compounds for antidepressant activity that do not cause the side effects of cognitive impairment, ataxia, potentiation of alcohol effects, and a tendency for tolerance and drug dependence, or that display these side effects only at a very low level. These method comprise:

a) screening compounds, optionally measuring the binding affinity of the compounds at GABA$_A$ receptors;

b) determining in vitro efficacy and EC$_{50}$ values for the compounds at cloned $\alpha_2\beta_3\gamma_2$ and $\alpha_3\beta_3\gamma_2$ receptors and comparing these values to in vitro efficacy and EC$_{50}$ values for the compounds determined at GABA$_A$ receptors that contain an $\alpha_1$ or $\alpha_5$ subunit; and c) selecting compounds having partial agonist character and that produce sufficiently low EC$_{50}$ values at $\alpha_2\beta_3\gamma_2$ and $\alpha_3\beta_3\gamma_2$ subtype receptors and display lower efficacy activity at GABA$_A$ subtype receptors that contain the $\alpha_1$ or $\alpha_5$ subunit. The compounds selected by this method have antidepressant activity.

The assay may include an assessment of the ability of the compound to mediate antidepressant effects in vivo without causing sedation. Animal models predictive of antidepressant effects and sedative effects can be used for the in vivo determination.

Thus, the invention presents methods for identifying compounds with antidepressant activity, i.e., selective antidepressant activity, (1) by examining the binding of a given compound at GABA$_A$ receptors and (2) by assessing the ability of the compound to potentiate GABA responses at a series of GABA$_A$ subtype receptors. The resulting values are then compared to a set of criteria termed the "Antidepressant Activity Range Profiler" (Table IV, below). The criteria given by the Antidepressant Activity Rang Profiler are used to identify compounds with antidepressant activity that have no or very minimal sedative effects. This activity profile comprises determinations of in vitro efficacy (agonist, inverse agonist or antagonist character) and EC$_{50}$ values at each of 4 GABA$_A$ subtype receptors. The activity profile needed for antidepressant activity is presented as a precise window of agonism and EC$_{50}$ values at each of these subtype receptors. The combination of determining efficacy and EC$_{50}$ values for a test compound is crucial as many compounds bind with high affinity at the benzodiazepine site without potentiating the GABA response at the appropriate subtype receptors. Furthermore, as noted previously, EC$_{50}$ values do not necessarily correlate with binding affinities or compound efficacies.

In certain embodiments, the conclusions drawn from the in vitro determinations may be confirmed by examining the in vivo effects of test compounds selected as having antidepressant activity using animal models for depression. It may also be desirable to verify that compounds identified by these methods do indeed possess the predicted favorable side effect profiles by examining the performance of the compounds in animal models known to be indicative of these side effects. Thus, the animal models may be used as an additional step of the assay to further refine the selection of compounds with selective antidepressant activity.

Hypnotics: With regard to hypnotics, a method of the invention involves optionally measuring the binding affinity of a compound at GABA$_A$ receptors having Ro15–1788 binding sites, and measuring the efficacy and EC$_{50}$ values of a compound at cloned $\alpha_2\beta_3\gamma_2$ and $\alpha_3\beta_3\gamma_2$ receptors and comparing these values with the activities and EC$_{50}$ values of the compound at cloned GABA$_A$ receptors containing the $\alpha_1$ or $\alpha_5$ subunits. Optionally, the ability of the compound to mediate hypnotic effects is assessed in vivo using an animal model established to be predictive of sedation, and whether the compound causes cognitive impairment may also be assessed in vivo by an animal model shown to be predictive of this effect.

Accordingly, this invention provides a method for identifying compounds with hypnotic activity that do not display the side effects of cognitive impairment, ataxia, potentiation of alcohol effects, and a tendency for tolerance and drug dependence or that display these side effects only at a very low level. This method comprises:

a) screening compounds, optionally measuring the binding affinity of the compounds at GABA$_A$ receptors;

b) measuring the EC$_{50}$ and in vitro efficacy values of the compounds at cloned $\alpha_2\beta_3\gamma_2$ and $\alpha_3\beta_3\gamma_2$ receptors and comparing these values to the EC$_{50}$ and in vitro efficacy values of the compounds that contain the $\alpha_1$ or $\alpha_5$ subunit; and c) selecting compounds with sufficiently low EC$_{50}$ values at $\alpha_2\beta_3\gamma_2$ and $\alpha_3\beta_3\gamma_2$ receptors, partial agonist activity at $\alpha_2\beta_3\gamma_2$ receptors and stronger partial agonist activity at $\alpha_3\beta_3\gamma_2$ receptors, that also display lower activity at GABA$_A$ subtype receptors that contain the $\alpha_1$ or $\alpha_5$ subunit as having hypnotic activity.

Alternatively, this assay may be performed without measuring the binding affinity of the compound or with the additional step of assessing the ability of the compound to mediate hypnotic effects in vivo without causing cognitive impairment via an animal model established to be predictive of sedation and an animal model predictive of cognitive impairment.

Thus, the invention provides methods for identifying compounds with hypnotic activity (1) by examining the binding of a given compound at GABA$_A$ receptors and (2) by assessing the ability of the compound to potentiate GABA responses at a series of GABA$_A$ subtype receptors. The resulting values are then compared to a set of empirically defined criteria termed the "Hypnotic Activity Range Profiler" (Table II, below). The criteria given by the Hypnotic Activity Range Profiler are used to identify compounds with sedative hypnotic activity that have no or very minimal side effects. This activity profile comprises measurements of in vitro efficacy (agonist, inverse agonist or antagonist character) and EC$_{50}$ values at each of 4 GABA$_A$ subtype receptors. The activity profile needed for hypnotic effects is presented as a precise window of agonism and EC$_{50}$ criteria at each of these subtype receptors. This well-defined activity profile requires partial agonist activity at subtype receptors containing the $\alpha_2$ and $\alpha_3$ subunits and lower agonist activity at other subtype receptors. The combination of determining efficacy and EC$_{50}$ of a test compound is crucial as many compounds bind with high affinity at the benzodiazepine site without potentiating the GABA response at the appropriate subtype receptors.

In certain embodiments, the conclusions drawn from the in vitro determinations may be confirmed by examining the in vivo efficacy of test compounds predicted to have hypnotic properties using animal models for evaluating sedative activity. It may also be desirable to verify that compounds identified by these methods possess the favorable side effect profiles by examining the performance of the compounds in animal models known to be predictive of these side effects. Thus, the animal models may be used as an additional step of the assay to further refine the selection of compounds with selective hypnotic activity.

Additional Disclosure

In a further aspect of the present invention, a method of providing pharmaceutical compounds to patients in need of cognition enhancement, hypnosis, anxiolysis, and/or antidepressant treatment (such patients including humans, pets, livestock, and other animals) is provided. In accordance with this method, compounds are obtained that have been identified as having anxiolytic activity, hypnotic activity, antidepressant activity or cognition enhancing activity in accordance with any of the novel screening, characterization, analysis or identification methods of the present invention. Preferably such screening, characterization, analysis or identification is carried out outside of the United States of America. Once such compounds have been obtained, they are tested, preferably in vivo, for toxicity and pharmacokinetic properties. At least one compound determined to have minimal toxic effects and to have useful pharmacokinetic properties is then selected for clinical development. By useful pharmacokinetic properties is meant pharmacokinetic properties known in the art to be useful for a compound having the particular activity of anxiolytic activity, hypnotic activity, antidepressant activity or cognition enhancing activity, as identified for each particular compound in accordance with any of the novel screening, characterization, analysis or identification methods of the present invention for each compound. By clinical development is meant those activities, including testing in patients, related to the development and submission of information under a United States Federal law which regulates the manufacture, use, or sale of drugs or veterinary products, such as the Federal Food Drug and Cosmetic Act and other applicable government laws and regulations pertaining thereto. The final step in this method is the offer for sale (preferably in the United States of America) for use as a drug or veterinary product of a pharmaceutical preparation (such as a pill, powder, inhalant, elixir, injectable solution, patch or suppository) comprising the compound.

DETAILED DESCRIPTION OF THE INVENTION

The invention provides methods for screening compounds for activity as antidepressants, cognitive enhancers, sedative hypnotics, or anxiolytics. Therapeutic compounds identified by these methods mediate effects through the benzodiazepine site of the GABA$_A$ receptor without eliciting side effects classically associated with compounds exhibiting such activity that act at this site.

Although optional, it is preferred that part b) of each method embodiment (as set forth below) will be conducted on compounds displaying sufficiently potent binding affinities as determined in part a) of the method.

In one aspect of each embodiment of the method, prior to determining an in vitro efficacy value for the test compound, the binding affinity of the compound is measured in cells expressing cloned $\alpha$, $\beta$, and $\gamma$ GABA$_A$ receptor subunits or in a cell membrane preparation of such cells.

In another embodiment, prior to determining the in vitro efficacy values for the test compound, the binding affinity of the test compound is determined in any tissue capable of expressing GABA$_A$ receptors containing Ro15–1788 binding sites or in a cell membrane preparation of any tissue capable of expressing GABA$_A$ receptors containing Ro15–1788 binding sites. In a preferred embodiment of the method, prior to determining in vitro efficacy values of the test compound, the binding affinity of the test compound is determined in rat spinal cord tissue or in a cell membrane preparation of rat spinal cord tissue.

In more preferred embodiments of the method, the binding affinity of a test compound is measured in rat cortex or in a cell membrane preparation of rat cortex.

In particularly preferred embodiments, the binding affinity of a test compound is determined in rat cortex or in a cell membrane preparation of rat cortex and the test compound is selected for further evaluation if it gives a K$_i$ value of <100 nM or, preferably, <50 nM or, most preferably, <30 nM.

In these embodiments, the binding affinity of a compound may be first determined by evaluating the ability of the compound to displace a radiolabeled compound, for example Ro15–1788 (Flumazenil), known to have high affinity at the benzodiazepine site.

The in vitro efficacy and EC$_{50}$ value of the test compound may be determined by measuring the chloride flux at the surface of a cell expressing the $\alpha,\beta$, and $\gamma$ subunits of the GABA$_A$ receptor in response to GABA by the two electrode voltage-clamp technique. While a variety of cells are suitable for use herein, the preferred cells used in this technique are Xenopus laevis oocytes that have been injected with non-polyadenylated cRNA coding for human derived $\alpha$, $\beta$ and γ GABA$_A$ subunits. The preferred form of the γ subunit is the normally expressed long form although an alternatively spliced form may be used.

A: Cognitive Enhancers: Cognitive enhancers identified by this method produce inverse agonist activity at the α1β2γ2 or α5β3γ2 GABAA subtype receptors and agonist activity at subtype receptors containing the α2 or α3 subunits of the possible subunit combinations for receptors containing α2 or α3 subunits, the most relevant are the α2β3γ2 and α3β3γ2 subtype receptors. Compounds selected according to the invention have EC$_{50}$ values of about 200 nM or less at the α1β2γ2 and α5β3γ2 GABA$_A$ subtype receptors and EC$_{50}$ values preferably of 150 nM or less at these receptors.

The criteria for screening compounds for cognitive enhancing activity are presented below.

In a preferred embodiment, after the binding affinity of the compound has been determined, in vitro efficacy and EC$_{50}$ value are determined for the test compound using cells expressing the α$_1$β$_2$γ$_2$ or α$_5$β$_3$γ$_2$ GABA$_A$ receptor subunit combinations. If the test compound produces >5% inverse agonist activity (<−5% efficacy), or preferably >10% inverse agonist activity (<−10% efficacy), at either the α$_1$β$_2$γ$_2$ or α$_5$β$_3$γ$_2$ GABA$_A$ receptors and gives EC$_{50}$ values of <200 nM, or more preferably <150 nM, at these subunit combinations, these efficacy values are compared to the in vitro efficacy values determined with cells expressing GABA$_A$ subtype receptors containing α$_2$β$_3$γ$_2$ or α$_3$β$_3$γ$_2$ subunits. Where the compound produces >5% or preferably >10% agonist activity at these subunits it is selected as having cognitive enhancing activity.

TABLE I

Cognitive Enhancer Activity Range Profiler

| K$_i$ RO15-1788 Rat cortex | EC$_{50}$/ efficacy at α$_1$β$_2$γ$_2$ | EC$_{50}$/ efficacy at α$_2$β$_2$γ$_2$ | EC$_{50}$/ efficacy at α$_3$β$_3$γ$_2$ | EC$_{50}$/ efficacy at α$_5$β$_3$γ$_2$ | animal behavior effects (positive effect/ side effect) |
|---|---|---|---|---|---|
| <30 nM | <150 nM/ <−10% or >+10% | any*/ >10% | any*/ >10% | <150 nM/ <−10% | positive effect in spatial water maze or step down passive avoidance/ little or no effect in seizure threshold tests, no effect in elevated plus maze model |

*A wide range of EC$_{50}$ values for the α$_2$β$_3$γ$_2$ and α$_3$β$_3$γ$_2$ subtype receptors is permitted. However, in practice, the "any/ >10%" criteria are used for compounds having EC$_{50}$ values at these subtypes lesser than 100 times the EC$_{50}$ values at the α$_1$β$_2$γ$_2$ or α$_5$β$_3$γ$_2$ subtype receptors. On the other hand, when the EC$_{50}$ value for a compound at either the α$_2$β$_3$γ$_2$ or the α$_3$β$_3$γ$_2$ subtype receptor is more than 100 times the EC$_{50}$ values for α$_1$β$_2$γ$_2$ or α$_5$β$_3$γ$_2$ subtype receptors, then <10% in vitro efficacy is acceptable.

Thus, methods of this invention comprise:
  a) screening compounds, optionally ones having a binding affinity less than 100 nM or preferably less than 30 nM at any GABA$_A$ receptor;
  b) determining the in vitro efficacy and EC$_{50}$ values for the compounds at cloned α$_1$β$_2$γ$_2$ and α$_5$β$_3$γ$_2$ receptors;
  c) determining in vitro efficacy and EC$_{50}$ values for the compounds at GABA$_A$ subtype receptors containing the α$_2$ or α$_3$ subunit; and
  d) selecting a compound having an EC$_{50}$ value determined in b) of less than 200 nM or preferably less than 150 nM, an efficacy value determined in b) of less than −5% (e.g., −6%, −10%, etc.) or preferably less than −10%, and an efficacy determined in c) of greater than 5% or, preferably, greater than 10%.

In preferred embodiments after the binding affinity of the compound has been determined, in vitro efficacy and EC$_{50}$ values for the test compound are measured at cells expressing the α$_1$β$_2$γ$_2$ or α$_5$β$_3$γ$_2$ GABA$_A$ receptor subunit combinations. If the test compound exhibits >5% inverse agonist activity (<−5% efficacy), or preferably >10% inverse agonist activity (<−10% efficacy), at either the α$_1$β$_2$γ$_2$ or the α$_5$β$_3$γ$_2$ GABA$_A$ receptor and gives EC$_{50}$ values of <200 nM, or more preferably <150 nM, at these subunit combinations, these values are compared to in vitro efficacy values determined using cells expressing GABA$_A$ subtype receptors containing α$_2$ or α$_3$ subunits. Compounds producing >5% or preferably >10% agonist activity at these subunits are selected as having cognitive enhancing activity.

In alternative embodiments, the method includes an in vivo evaluation of the ability of the compound to mediate cognitive enhancement without causing proconvulsant effects. This is done using animal models predictive of cognition enhancement and of proconvulsant activity. Compounds that produce a statistically significant effect in an animal model predictive of cognitive enhancement are considered to be cognitive enhancing. Compounds that give either a decrease in seizure threshold of less than 25% in the presence of a seizure inducing drug or no significant effect at the p=0.05 level are identified as lacking proconvulsant activity.

In addition, the method may include an evaluation of whether the compound produces anxiogenic effects. This is done using an animal model predictive of anxiogenesis. A compound that gives no statistically significant effect in the animal model predictive of anxiogenesis is identified as lacking anxiogenic activity.

In accordance with another alternative embodiment of the method, the cognitive enhancing properties of the compound are determined without measuring the binding affinity of the compound but with the additional step of measuring the ability of the compound to mediate cognitive enhancement in vivo without proconvulsant effects, via an animal model predictive of cognition enhancement and an animal model predictive of proconvulsant activity.

In accordance with yet another alternative embodiment of the method, the cognitive enhancing properties of the compound are determined without measuring the binding affinity of the compound but with the additional step of measuring the ability of the compound to mediate cognitive enhancement in vivo without proconvulsant effects and without anxiogenic effects, via an animal model predictive of cognition enhancement, an animal model predictive of proconvulsant activity, and an animal model predictive of anxiogenesis, respectively.

The spatial water maze and step-down passive avoidance models are suitable models for in vivo determinations of cognition enhancement. The bicuculline or PTZ seizure threshold tests are suitable for use in vivo to determine proconvulsant activity. The elevated plus maze model is an example of a model that may be used in vivo to predict anxiogenic activity.

B: Hypnotics: Hypnotic compounds identified by this method mediate effects through the benzodiazepine site of the $GABA_A$ receptor either without eliciting the side effects classically associated with compounds that act at this site or elicit these side effects only to very low degree. These side effects include cognitive impairment, ataxia, potentiation of alcohol effects, and a tendency for tolerance and drug dependence. More specifically, compounds identified as hypnotics by this method show partial agonist activity at $\alpha_2\beta_3\gamma_2$ receptors, stronger partial agonist activity at $\alpha_3\beta_3\gamma_2$ $GABA_A$ subtype receptors, and lower activity at subtype receptors containing the $\alpha_1$ or $\alpha_5$ subunits. Of the possible subunit combinations for receptors containing $\alpha_1$ or $\alpha_5$ subunits the most relevant are the $\alpha_1\beta_2\gamma_2$ and $\alpha_5\beta_3\gamma_2$ subtype receptors. Additionally, compounds useful for any of these indications must have $EC_{50}$ values of 200 nM or less at the $\alpha_2\beta_3\gamma_2$ and $\alpha_3\beta_3\gamma_2$ $GABA_A$ subtype receptors and preferably should exhibit $EC_{50}$ values of 150 nM or less at these receptors.

The criteria for selecting a compound as having hypnotic properties are presented below in tabular form.

d) selecting a compound having an $EC_{50}$ value as determined in b) of less than 200 nM, or preferably less than 150 nM, and an efficacy value for the $\alpha_2\beta_3\gamma_2$ receptor of greater than 10%, or preferably greater than 20%, an efficacy value for the $\alpha_3\beta_3\gamma_2$ receptor of greater than 50%, or preferably greater than 60%, an efficacy value for the receptor containing the $\alpha_1$ subunit of less than 50%, or preferably less than 45%, and an efficacy value for the receptor containing the o subunit of less than 45%, or preferably less than 40%.

In preferred embodiments of the invention, after the binding affinity of the compound has been determined, the in vitro efficacy and $EC_{50}$ of the test compound are measured using cells expressing the $\alpha_2\beta_3\gamma_2$ $GABA_A$ receptor subunit combination and cells expressing the $\alpha_3\beta_3\gamma_2$ $GABA_A$ receptor subunit combination. If the test compound exhibits $EC_{50}$ values of <200 nM or more preferably <150 nM at these subtype receptors, partial agonist activity at $\alpha_2\beta_3\gamma_2$ receptors and stronger partial agonist activity at $\alpha_3\beta_3\gamma_2$ receptors, these values are compared to the in vitro efficacy and $EC_{50}$ values of cells expressing subtype receptors that contain the $\alpha_1$ or $\alpha_5$ subunits. If the compound also exhibits lower activity at receptors containing $\alpha_1$ or $\alpha_5$ subunits, it is selected as having hypnotic properties.

In other preferred embodiments, after the binding affinity of the compound has been determined, the in vitro efficacy and $EC_{50}$ values of the test compound are measured using cells expressing the $\alpha_2\beta_3\gamma_2$ $GABA_A$ receptor subunit combination and cells expressing the $\alpha_3\beta_3\gamma_2$ $GABA_A$ receptor subunit combinations. If the test compound gives $EC_{50}$ values of <200 nM or more preferably <150 nM at these subunit combinations, >10% or preferably >20% agonist activity at the $\alpha_2\beta_3\gamma_2$ subtype receptor, and 50% or preferably >60% agonist activity at the $\alpha_3\beta_3\gamma_2$ subtype receptor,

TABLE II

Hypnotic Activity Range Profiler

| $K_i$ RO15-1788 Rat cortex | $EC_{50}$/efficacy at $\alpha_1\beta_2\gamma_2$ | $EC_{50}$/efficacy at $\alpha_2\beta_3\gamma_2$ | $EC_{50}$/efficacy at $\alpha_3\beta_3\gamma_2$ | $EC_{50}$/efficacy at $\alpha_5\beta_3\gamma_2$ | animal behavior effects (positive effect/side effect) |
|---|---|---|---|---|---|
| <30 nM | any*/<45% | <150 nM/>20% | <150 nM/>60% | any*/<40% | positive effect in spontaneous locomotor activity model/limited effect in passive avoidance or spatial water maze model |

*A wide range of $EC_{50}$ values at the $\alpha_1\beta_2\gamma_2$ and $\alpha_5\beta_3\gamma_2$ subtype receptors is permitted in practice, however, the "any*/<45%" and "any/<40%" criteria are preferably used for compounds having $EC_{50}$ values at these subtypes less than 100 times the $EC_{50}$ values at the $\alpha_2\beta_3\gamma_2$ and $\alpha_3\beta_3\gamma_2$ subtype receptors. On the other hand, when the $EC_{50}$ values of the compound at the $\alpha_1\beta_2\gamma_2$ or $\alpha_5\beta_3\gamma_2$ subtype receptor are greater than 100 times greater the $EC_{50}$ values at the $\alpha_2\beta_3\gamma_2$ or $\alpha_3\beta_3\gamma_2$ subtype receptors, then >45% in vitro efficacy for the $\alpha_1\beta_2\gamma_2$ subtype receptor or >40% in vitro efficacy for the $\alpha_5\beta_3\gamma_2$ subtype receptor is acceptable.

Thus in broad aspect, the methods of this invention comprise:
a) screening compounds, optionally, selecting compounds having a binding affinity less than 100 nM at any $GABA_A$ receptor;
b) determining in vitro efficacy and $EC_{50}$ values for the compounds at cloned $\alpha_2\beta_3\gamma_2$ and $\alpha_3\beta_3\gamma_2$ receptors;
c) determining in vitro efficacy and $EC_{50}$ values for the compounds at $GABA_A$ subtype receptors containing the $\alpha_1$ or $\alpha_5$ subunit;

these values are compared to the in vitro efficacy and $EC_{50}$ values in cells expressing the $GABA_A$ receptors containing $\alpha_1$ or $\alpha_5$ subunits. If the compound also exhibits <50% or preferably <45% agonist activity at $GABA_A$ receptor containing the $\alpha_1$ subunit and exhibits <45% or preferably <40% agonist activity at $GABA_A$ receptor containing the $\alpha_5$ subunit, it is selected as having hypnotic properties.

In more preferred embodiments, after the binding affinity of the compound has been determined, in vitro efficacy and $EC_{50}$ values of the test compound are measured using cells expressing the $\alpha_2\beta_3\gamma_2$ GABA$_A$ receptor subunit combination and cells expressing the $\alpha_3\beta_3\gamma_2$ GABA$_A$ receptor subunit combination. If the test compound gives EC$_{50}$ values <200 nM or more preferably <150 nM at these subunit combinations, >10% or preferably >20% agonist activity at the $\alpha_2\beta_3\gamma_2$ subtype receptor, and >50% or preferably >60% agonist activity at the $\alpha_3\beta_3\gamma_2$ subtype receptor, these values are compared to the in vitro efficacy and EC$_{50}$ values at cells expressing $\alpha_1\beta_2\gamma_2$ and $\alpha_5\beta_3\gamma_2$ subtype receptors. If the compound also exhibits <50% or preferably <45% agonist activity at the $\alpha_1\beta_2\gamma_2$ subtype receptor or exhibits <45% or preferably <40% agonist activity at the $\alpha_1\beta_2\gamma_2$ subtype receptor GABA$_A$, it is selected as having hypnotic properties.

In alternative embodiments, the method includes measuring the ability of the compound to mediate hypnotic effects in vivo without causing cognitive impairment. This is accomplished using an animal model predictive of a compound's ability to cause hypnotic effects and an animal model developed to be predictive of cognitive impairment. A compound that shows a statistically significant effect in the animal model predictive of sedation and no statistically significant effect in the animal model predictive of cognitive impairment is identified as having hypnotic properties.

Suitable in vivo animal models include the spontaneous locomotor model for predicting hypnotic effects, and the step-down passive avoidance model or the spatial water maze model determining cognitive impairment.

C: Anxiolytics: Methods are provided for identifying selective anxiolytic compounds. Therapeutic compounds identified by these methods mediate effects through the benzodiazepine site of the GABA$_A$ receptor either without eliciting the side effects classically associated with compounds that act at this site or elicit these side effects only to a very low degree. These side effects include cognitive impairment, sedation, ataxia, potentiation of alcohol effects, and a tendency for tolerance and drug dependence. More specifically, compounds identified as selective anxiolytics by this method show agonist activity at the $\alpha_2\beta_3\gamma_2$ and $\alpha_3\beta_3\gamma_2$ GABA$_A$ subtype receptors and lower to no agonist activity at subtype receptors containing the $\alpha_1$ or $\alpha_5$ subunits. Of the possible subunit combinations for receptors containing $\alpha_1$ or $\alpha_5$ subunits, the most relevant are the $\alpha_1\beta_2\gamma_2$ and $\alpha_5\beta_3\gamma_2$ subtype receptors. Additionally, compounds useful for any of these indications must have EC$_{50}$ values of 200 nM or less at the $\alpha_2\beta_3\gamma_2$ and $\alpha_3\beta_3\gamma_2$ GABA$_A$ subtype receptors and preferably should exhibit EC$_{50}$ values of 150 nM or less at these receptors.

The criteria for selecting a compound as having anxiolytic properties are presented below in tabular form.

TABLE III

Anxiolytic Activity Range Profiler

| K$_i$ Ro15-1788 Rat cortex | EC$_{50}$/ efficacy at $\alpha_1\beta_2\gamma_2$ | EC$_{50}$/ efficacy at $\alpha_2\beta_3\gamma_2$ | EC$_{50}$/ efficacy at $\alpha_3\beta_3\gamma_2$ | EC$_{50}$/ efficacy at $\alpha_5\beta_3\gamma_2$ | animal behavior effects (positive effect/side effect) |
| --- | --- | --- | --- | --- | --- |
| <30 nM | any*/<20% | <150 nM/ >30% | <150 nM/ >30% | any*/<20% | positive effect in elevated plus maze/ no effect in spontaneous locomotor activity model |

*A wide range of EC$_{50}$ values at the $\alpha_1\beta_2\gamma_2$ and $\alpha_5\beta_3\gamma_2$ subtype receptors is permitted. In practice however, the "any/<20%" criteria are preferably used for compounds having EC$_{50}$ values at these subtypes less than 100 times the EC$_{50}$ values at the $\alpha_2\beta_3\gamma_2$ and $\alpha_3\beta_3\gamma_2$ subtype receptors. On the other-hand, when the EC$_{50}$ values of a compound at the $\alpha_1\beta_2\gamma_2$ or $\alpha_5\beta_3\gamma_2$ subtype receptors are greater than 100 times the EC$_{50}$ values at the $\alpha_2\beta_3\gamma_2$ or $\alpha_3\beta_3\gamma_2$ subtype receptors, >20% in vitro efficacy is acceptable.

Thus, in a broad aspect the invention comprises:
 a) screening compounds, optionally compounds having a binding affinity less than 100 nM at any GABA$_A$ receptor;
 b) measuring in vitro efficacy and EC$_{50}$ values for the compounds at cloned $\alpha_2\beta_2\gamma_2$ and $\alpha_3\beta_3\gamma_2$ receptors;
 c) measuring in vitro efficacy and EC$_{50}$ values for the compounds at GABA$_A$ subtype receptors containing the $\alpha_1$ or $\alpha_5$ subunit; and
 d) selecting a compound having an EC$_{50}$ as measured in b) of less than 200 nM and an efficacy value as measured in b) is greater than the efficacy values measured in c.

In preferred embodiments, after the binding affinity of the compound has been determined, the in vitro efficacy and EC$_{50}$ of the test compound are measured at cells expressing the $\alpha_2\beta_3\gamma_2$ and $\alpha_3\beta_3\gamma_2$ GABA$_A$ receptor subunit combinations. If the test compound exhibits any agonist activity and gives EC$_{50}$ values <200 nM, or more preferably <150 nM, at these subunit combinations, these values are compared to the in vitro efficacies at cells expressing GABA$_A$ subtype receptors containing $\alpha_1$ or $\alpha_5$ subunits. If the compound exhibits lower or no activity at these latter subunits, it is identified as having anxiolytic properties.

In other preferred embodiments, after the binding affinity of the compound has been determined, the in vitro efficacy and EC$_{50}$ of the test compound are measured using cells expressing the $\alpha_2\beta_3\gamma_2$ and $\alpha_3\beta_3\gamma_2$ GABA$_A$ receptor subunit combinations. If the test compound exhibits any agonist activity and gives EC$_{50}$ values of <200 nM, or more preferably <150 nM, at these subunit combinations, these values are compared to the in vitro efficacy in cells expressing the $\alpha_1\beta_2\gamma_2$ GABA$_A$ receptor subunit combination. If the compound exhibits lower to no activity at this subunit it is identified as having non-sedating anxiolytic properties.

In further embodiments, after the binding affinity of the compound has been determined, the in vitro efficacy and EC$_{50}$ of the test compound are measured using cells expressing the $\alpha_2\beta_3\gamma_2$ and $\alpha_3\beta_3\gamma_2$ GABA$_A$ receptor subunit combinations. If the test compound exhibits agonist activity and gives EC$_{50}$ values of <200 nM, or more preferably <150 nM, at these subunit combinations, the efficacy values are compared to in vitro efficacy values using cells expressing the $\alpha_1\beta_2\gamma_2$ and $\alpha_5\beta_3\gamma_2$ GABA$_A$ receptor subunit combinations. If the compound exhibits lower to no activity at these subunits it is identified as having non-sedating anxiolytic properties.

In still other embodiments, after the binding affinity of the compound has been determined, in vitro efficacy and EC$_{50}$ values for the test compound are measured in cells expressing the $\alpha_2\beta_3\gamma_2$ and $\alpha_3\beta_3\gamma_2$ GABA$_A$ receptor subunit combinations. If the test compound gives >30% potentiation (i.e., increase) of the GABA response and EC$_{50}$ values of <200 nM, or more preferably <150 nM at these subunit combinations, the efficacy values are compared to the in vitro efficacies determined using cells expressing GABA$_A$ subtype receptors containing $\alpha_1$ or $\alpha_5$ subunits. If the compound exhibits lower to no activity (efficacy) at these subunits it is identified as having non-sedating anxiolytic properties.

In yet other embodiments, after the binding affinity of the compound has been determined, in vitro efficacy and EC$_{50}$ values for the test compound are measured using cells expressing the $\alpha_2\beta_3\gamma_2$ and $\alpha_3\beta_3\gamma_2$ GABA$_A$ receptor subunit combinations. If the test compound produces >30% potentiation of the GABA response and EC$_{50}$ values of <200 nM, or more preferably <150 nM, at these subunit combinations, these efficacy values are compared to the in vitro efficacy values determined using cells expressing the $\alpha_1\beta_2\gamma_2$ GABA$_A$ receptor subunit combination. If the compound exhibits lower to no activity efficacy at this subunit, it is identified as having non-sedating anxiolytic properties.

In more preferred embodiments, after the binding affinity of the compound has been determined, in vitro efficacy and EC$_{50}$ values for the test compound are measured using cells expressing the $\alpha_2\beta_3\gamma_2$ and $\alpha_3\beta_3\gamma_2$ GABA$_A$ receptor subunit combinations. If the test compound produces >30% potentiation of the GABA response and EC$_{50}$ values of <200 nM, or more preferably <150 nM, at these subunit combinations, these values are compared to the in vitro efficacy values measured with cells expressing the $\alpha_1\beta_2\gamma_2$ and $\alpha_5\beta_3\gamma_2$ GABA$_A$ receptor subunit combinations. If the compound produces lower to no efficacy activity at these subunits, it is identified as having non-sedating anxiolytic properties.

In particularly preferred embodiments, after the binding affinity of the compound has been determined, in vitro efficacy and EC$_{50}$ values for the test compound are measured using cells expressing the $\alpha_2\beta_3\gamma_2$ and $\alpha_3\beta_3\gamma_2$ GABA$_A$ receptor subunit combinations. If the test compound produces >30% potentiation of the GABA response and EC$_{50}$ values of <150 nM at these subunit combinations, the efficacy values are compared to in vitro efficacy measured using cells expressing the $\alpha_1\beta_2\gamma_2$ and $\alpha_5\beta_3\gamma_2$ GABA$_A$ receptor subunit combinations. If the compound gives <20% potentiation of the GABA response at these latter subunits, it is identified as having non-sedating anxiolytic properties.

In alternative embodiments, the method includes the additional step of measuring the ability of the compound to mediate anxiolytic effects in vivo without causing sedation. This is accomplished using animal models established to be predictive of anxiety and sedative effects. A compound that shows a statistically significant effect in the animal model predictive of anxiety and no statistically significant effect in the animal model predictive of sedative effects is identified as having non-sedating anxiolytic properties.

Suitable in vivo animal models include the elevated plus maze model for predicting anxiolytic activity and the spontaneous locomotor activity model to determine sedative effects.

Antidepressants: A method is provided for identifying antidepressant compounds. Therapeutic compounds identified by this method act through the benzodiazepine site of the GABA$_A$ receptor without eliciting the side effects classically associated with compounds that bind at this site. Alternatively, these compounds elicit the side effects only to a very low degree. These side effects include cognitive impairment, sedation, ataxia, potentiation of alcohol effects, and a tendency for tolerance and drug dependence. More specifically, compounds identified as antidepressants by this method show agonist activity at the $\alpha_2\beta_3\gamma_2$ and $\alpha_3\beta_3\gamma_2$ GABA$_A$ subtype receptors and lower or no agonist activity at subtype receptors containing the $\alpha_1$ or $\alpha_5$ subunits of the possible subunit combinations for receptors containing $\alpha_1$ or $\alpha_5$ subunits, preferred for use herein are the $\alpha_1\beta_2\gamma_2$ and $\alpha_5\beta_3\gamma_2$ subtype receptors. Compounds useful for any of these indications must produce EC$_{50}$ values of 200 nM or less at the $\alpha_2\beta_3\gamma_2$ and $\alpha_3\beta_3\gamma_2$ GABA$_A$ subtype receptors and preferably should exhibit EC$_{50}$ values of 150 nM or less at these receptors.

The preferred criteria for screening for compounds having antidepressant activity are presented in the table below.

TABLE IV

| | Antidepressant Activity Range Profiler | | | | |
|---|---|---|---|---|---|
| K$_i$ RO15-1788 Rat cortex | EC$_{50}$/ efficacy at $\alpha_1\beta_2\gamma_2$ | EC$_{50}$/ efficacy at $\alpha_2\beta_3\gamma_2$ | EC$_{50}$/ efficacy at $\alpha_3\beta_3\gamma_2$ | EC$_{50}$/ efficacy at $\alpha_5\beta_3\gamma_2$ | animal behavior effects (positive effect/ side effect) |
| <30 nM | any*/<20% | <150 nM/ >30% | <150 nM/ >30% | any*/<20% | positive effect Porsolt swim test/ no effect in spontaneous locomotor activity model |

*A wide range of EC$_{50}$ values for the $\alpha_1\beta_2\gamma_2$ and $\alpha_5\beta_3\gamma_2$ subtype receptors is permitted. In practice, however, the "any/<20%" criteria are used for compounds having EC$_{50}$ values at these subtypes less than 100 times the EC$_{50}$ values at the $\alpha_2\beta_3\gamma_2$ and $\alpha_3\beta_3\gamma_2$ subtype receptors. On the other hand, when the EC$_{50}$ value for the compound at either the $\alpha_1\beta_2\gamma_2$ or the $\alpha_5\beta_3\gamma_2$ subtype receptor is greater than 100 times the EC$_{50}$ values for either the $\alpha_2\beta_3\gamma_2$ or the $\alpha_3\beta_3\gamma_2$ subtype receptors, then >20% in vitro efficacy is acceptable.

Thus, the method of this invention comprises:

a) screening compounds, optionally compounds having a binding affinity less than 100 nM at any GABA$_A$ receptor;

b) determining in vitro efficacy and EC$_{50}$ values for the compounds at cloned $\alpha_2\beta_3\gamma_2$ and $\alpha_3\beta_3\gamma_2$ receptors;

c) determining in vitro efficacy and EC$_{50}$ values for the compounds at GABA$_A$ subtype receptors containing an $\alpha_1$ or $\alpha_5$ subunit; and d) selecting a compound having an $EC_{50}$ as determined in b) of less than 200 nM and an efficacy value as determined in b) greater than the efficacy value measured in c.

In preferred embodiments, after the binding affinity of the compound has been determined, in vitro efficacy and $EC_{50}$ values for the test compound are measured using cells expressing the $\alpha_2\beta_3\gamma_2$ and $\alpha_3\beta_3\gamma_2$ $GABA_A$ receptor subunit combinations. If the test compound exhibits any agonist activity and produces $EC_{50}$ values of <200 nM or, more preferably, <150 nM at these subunit combinations these values are compared to in vitro efficacy values determined using cells expressing $GABA_A$ subtype receptors containing $\alpha_1$ or $\alpha_5$ subunits. Compounds giving lower or no efficacy activity at the $\alpha_1$ or $\alpha_5$ subunits are selected as having antidepressant properties.

In a preferred aspect, the in vitro efficacy and $EC_{50}$ values are determined for the test compound using $\alpha_2\beta_3\gamma_2$ and $\alpha_3\beta_3\gamma_2$ $GABA_A$ receptor subunit combinations. If the test compound exhibits agonist activity and $EC_{50}$ values <200 nM or more preferably <150 nM at these subunit combinations, these values are compared to in vitro efficacy values determined with cells expressing the $\alpha_1\beta_2\gamma_2$ $GABA_A$ receptor subunit combination. Where the compound exhibits lower or no efficacy activity at the $\alpha_1\beta_2\gamma_2$ subunit, it is identified as having antidepressant properties.

In more preferred aspect, the in vitro efficacy and $EC_{50}$ values determined for the test compound using cells expressing the $\alpha_2\beta_3\gamma_2$ and $\alpha_3\beta_3\gamma_2$ $GABA_A$ receptor subunit combinations are compared to in vitro efficacy values determined using cells expressing the $\alpha_1\beta_2\gamma_2$ and $\alpha_5\beta_3\gamma_2$ $GABA_A$ receptor subunit combinations combination. Where the compound exhibits lower to no efficacy activity at both the $\alpha_1\beta_2\gamma_2$ and $\alpha_5\beta_3\gamma_2$ subunits, it is identified as having antidepressant properties.

In these embodiments, agonist activity is preferably defined as producing an efficacy value of >30% potentiation of the GABA response. Thus, in preferred embodiments of the invention if the test compound exhibits >30% potentiation of the GABA response at the $\alpha_2\beta_3\gamma_2$ and $\alpha_3\beta_3\gamma_2$ receptor subunits, and $EC_{,5}$ values of <200 nM or, more preferably <150 nM, at these subunit combinations, these values are compared to the in vitro efficacy at cells expressing the $\alpha_1\beta_2\gamma_2$ $GABA_A$ receptor subunit combination. Where the compound exhibits lower to no efficacy (agonist) activity at the $\alpha_1\beta_2\gamma_2$ subunit, it is identified as having antidepressant properties.

Particularly preferred embodiments comprise: determining the binding affinity of the compound for $GABA_A$ receptors determining in vitro efficacy and $EC_{50}$ values for the test compound with cells expressing the $\alpha_2\beta_3\gamma_2$ and $\alpha_3\beta_3\gamma_2$ $GABA_A$ receptor subunit combinations. Where the test compound produces >30% potentiation of the GABA response (i.e., agonist activity) and $EC_{50}$ values of <200 nM or, more preferably <150 nM, at these subunit combinations, these efficacy values are compared to in vitro efficacy values determined using cells expressing the $\alpha_1\beta_2\gamma_2$ and $\alpha_5\beta_3\gamma_2$ $GABA_A$ receptor subunit combinations. Where the compound exhibits <20% potentiation of the GABA response at the $\alpha_1\beta_2\gamma_2$ and $\alpha_5\beta_3\gamma_2$ subunits, it is identified as having antidepressant properties.

In alternative embodiments, the method includes, an in vivo evaluation of the ability of the compound to mediate antidepressant effects without causing sedation. This is done using animal models predictive of antidepressant activity and sedation. A compound that produces a statistically significant effect in an animal model predictive of antidepressant activity and no statistically significant effect in an animal model predictive of sedative effects is identified as having antidepressant properties.

Suitable in vivo animal models include the Porsolt swim test for predicting antidepressant activity and the spontaneous locomotor activity model for determining sedative effects.

In the forgoing embodiments and in the claims, any of the various criteria presented for characterizing each of hypnotic, antidepressant, anxiolytic or cognition enhancing properties (including those set forth in the various dependent claims submitted herewith regarding a particular one of such properties) may be applied in association with each aspect or embodiment of the invention concerning the characterization of that particular property and to each of the various independent claims submitted herewith regarding the characterization of that particular property.

The methods of the present invention are illustrated further by the following examples, which are not to be construed as limiting the invention in scope or spirit to the specific procedures and compounds described in them.

EXAMPLES

Example 1

Binding Assays

A preferred method for discovery of compounds that bind with high affinity to $GABA_A$ receptors is a competition binding assay. Rat cortex membranes are prepared by homogenizing one or two previously frozen rat cortexes in 30 ml of 25 mM Tris Buffer, pH 7.4. The homogenate is centrifuged for 10 minutes at 500×g. The supernatant is then transferred to a clean centrifuge tube and the pellet discarded. The supernatant is spun for 20 minutes at 48,000×g. The supernatant from this spin is discarded and the pellet is resuspended in 30 ml of 25 mM Tris Buffer, pH 7.4 and centrifuged for an additional 10 minutes at 48,000×g. The supernatant from the final spin is discarded and the membrane pellet is resuspended in 100 mL Tris buffer per gram of cortex used.

The cortex membrane preparation is used to perform either percent inhibition or competition binding assays. In order to determine percent inhibition 300 µl of resuspended membranes are mixed with 200 µl $^3$H labeled Ro15–1788 (final concentration 2.5 nM) and incubated for 1 hour on ice in the presence of 2 µl test compound in DMSO (final concentration 4 µM). Membranes are harvested onto untreated filtermats. The filtermats are dried and the $^3$H Ro15–1788 signal is counted in a scintillation counter. Nonspecific binding is determined by displacement of $^3$H Ro15–1788 with 10 µM Diazepam (RBI) or any other compound known to bind tightly at the benzodiazepine site.

For any test compound exhibiting a favorable percent inhibition a competition binding curve is obtained and a $K_i$ value is calculated. Generally, up to 11 points spanning the compound concentration range from $10^{-12}$ M to $10^{-5}$ M are obtained per curve by the same method as for the percent inhibition assay. $K_i$ values are calculated according to the Cheng-Prussof equation. Those compounds that exhibit $K_i$ values in the desired range are submitted for efficacy testing.

Example 2

Electrophysiology Assays

The efficacy profile of compounds of this invention is determined by the following electrophysiological assay for $GABA_A$ receptor activity.

Assays are carried out as described previously in White and Gurley, 1995 and White, et al., 1995. Xenopus laevis oocytes are enzymatically isolated and injected with non-polyadenylated cRNA for human derived α, β and γ GABA$_A$ subunits, respectively. In more preferred embodiments cRNA for the $\alpha_1\beta_2\gamma_2$, $\alpha_2\beta_3\gamma_2$, $\alpha_3\beta_3\gamma_2$, and $\alpha_5\beta_3\gamma_2$ subunit combinations are injected. Only one of these subunit combinations is injected per cell. For each subunit combination, sufficient message is injected to result in current amplitudes of >10 nA when 1 μM GABA is applied. Electrophysiological recordings are carried out using the two electrode voltage-clamp technique at a membrane holding potential of −70 mV.

Compounds are evaluated against a GABA concentration that evokes <10% ($EC_{10}$) of the maximal evocable GABA current. Each oocyte is exposed to increasing concentrations of compound in order to evaluate a concentration/effect relationship. Compound efficacy is expressed as a percent-change in current amplitude: $100*((Ic/I)-1)$, where Ic is the GABA evoked current amplitude observed in the presence of compound and I is the GABA evoked current amplitude observed in the absence of compound.

Specificity of a compound for the Ro15–1788 site is determined following completion of the concentration/effect curve. After washing the oocyte sufficiently to remove previously applied compound, the oocyte is exposed to GABA and 1 μM Ro15–1788, followed by exposure to GABA, 1 μM Ro15–1788, and compound. Percent change due to addition of compound is calculated as described above. Any percent change observed in the presence of Ro15–1788 is subtracted from the percent changes in current amplitude observed in the absence of 1 μM Ro15–1788. These net values are used for the calculation of average activity and $EC_{50}$ values.

To evaluate average activity and $EC_{50}$ values, the concentration/effect data are averaged across cells and fit to the logistic equation. Average values are reported as mean±standard error. In the preferred embodiment, anxiolytic compounds should exhibit an activity profile of <20% agonist activity at the $\alpha_1\beta_2\gamma_2$ and $\alpha_5\beta_3\gamma_2$ subunit combinations and >30% agonist activity at the $\alpha_2\beta_3\gamma_2$ and $\alpha_3\beta_3\gamma_2$ subunit combinations and $EC_{50}$ values <150 nM. Preferred hypnotic compounds exhibit an activity profile of >20% agonist activity at the $\alpha_2\beta_3\gamma_2$ subtype receptor, >60% agonist activity at the $\alpha_3\beta_3\gamma_2$ subtype receptor, <45% agonist activity at the $\alpha_1\beta_2\gamma_2$ subtype receptor, and <40% activity at the $\alpha_5\beta_3\gamma_2$ subunit combinations and $EC_{50}$ values of <150 nM at the $\alpha_2\beta_3\gamma_2$ and $\alpha_3\beta_3\gamma_2$ constructs. Preferred antidepressant compounds exhibit an activity profile of <20% agonist activity at the $\alpha_1\beta_2\gamma_2$ and $\alpha_5\beta_3\gamma_2$ subunit combinations, >30% agonist activity at the $\alpha_2\beta_3\gamma_2$ and $\alpha_3\beta_3\gamma_2$ subunit combinations, and $EC_{50}$ values of <150 nM at the $\alpha_2\beta_3\gamma_2$ and $\alpha_3\beta_3\gamma_2$ constructs. Preferred cognitive enhancing compounds produce an efficacy profile of >10% inverse agonist activity (<−10% efficacy) at the $\alpha_1\beta_2\gamma_2$ or $\alpha_5\beta_3\gamma_2$ subtype receptors, >10% agonist activity at the $\alpha_2\beta_3\gamma_2$ and $\alpha_3\beta_3\gamma_2$ subunit combinations, and produce $EC_{50}$ values of <150 nM at the $\alpha_1\beta_2\gamma_2$ and $\alpha_5\beta_3\gamma_2$ subtype receptors. The modulatory effect on the GABA current amplitude is near maximal for all subtype receptors studied.

Example 3

Animal Behavior Methods

To verify that compounds identified as selective anxiolytics, hypnotics, antidepressants, or cognitive enhancers by this method mediate these effects it is preferable to examine the performance of some such compounds in vivo. A series of animal models, most preferably rat models, are employed for this purpose.

It has been established that the elevated plus maze model can be used to determine anxiolytic efficacy of compounds. Side effects associated with anxiolytic compounds can be ascertained from a variety of animal models. The spontaneous locomotor activity model can be used to determine whether test compounds cause sedation.

Spontaneous locomotor activity has been established as a measure of hypnotic effect. Among the most common side effects of currently prescribed sedative hypnotics are learning and memory deficits or cognitive impairment. Consequently, one of the goals of the sedative hypnotic program has been to develop a sedative hypnotic compound with minimal side effects of this nature. The step-down passive avoidance and spatial water maze paradigms can be used to determine whether test compounds cause learning and memory deficits.

The Porsolt swim test has been established as a measure of determining antidepressant activity of compounds. Side effects associated with antidepressant compounds can be ascertained from a variety of animal models. For example, the spontaneous locomotor activity model may be used to determine whether test compounds cause sedation.

The spatial water maze model or the step-down passive avoidance model may be used to measure cognitive enhancement. Proconvulsant activity and anxiogenic effects are the side effects of greatest concern for compounds that act as cognitive enhancers via the benzodiazepine site. The bicuculline seizure threshold or the PTZ seizure threshold tests may be used to determine whether cognition enhancing compounds are proconvulsant; the elevated plus maze may be used to determine whether such compounds are anxiogenic.

The absence of side effects for a compound that shows in vivo efficacy is indicative that the compound not only has the desired activity but that it is also a selective compound. A statistically significant effect in the spatial water maze, step-down passive avoidance, spontaneous locomotor activity, Porsolt swim test, or the elevated plus maze models is defined as p<0.05 using a valid parametric statistical test. Likewise, no statistically significant effect is defined in these models as p>0.05 using a valid parametric statistical test. No statistically significant effect for either of the seizure threshold models is defined as a decrease of less than 25% in the seizure threshold in the presence of a seizure inducing drug or a result that is not significant at the p<0.05 level.

a. Elevated Plus Maze

The elevated plus maze model capitalizes on rats' innate fear of open, elevated places. The test apparatus is an elevated plus maze consisting of two open arms and two closed arms. A rat will naturally chose to spend more time on the closed arms of the maze than on the open arms but that if an efficacious anxiolytic compound is administered to the rat prior to the test the amount of time the rat spends in the open arms is increased.

Test compound is administered IV in a 50% PEG (polyethylene glycol) vehicle 5 minutes prior to the test session. A range of compound doses is typically used and 8–10 rats are tested at each dose. The rat is placed in the center of the maze facing one of the open arms. The animal's locomotion is tracked over a five minute test session using photocells interfaced to a computer. The computer measures the number of entries into each arm and the time spent on each arm. An anxiolytic effect in the elevated plus maze model is defined by an increase in the percentage of time spent on the open arms in compound versus vehicle treated animals.

b. Spontaneous Locomotor Activity

Spontaneous locomotor activity can be measured to determine sedative effects of compounds. Locomotor activity is measured in eight computerized Digiscan-16 Animal Activity Monitors (Omnitech Electronics, Columbus, Ohio) equipped with 48 infrared photocell emitters and detectors. Each box is constructed of Plexiglas sides and floor. Horizontal activity, is detected by a set of horizontal sensors on the front to back walls and a second group of sensors on the side to side walls located 5 cm above the cage floor. Vertical activity is detected by a third set of sensors on the side to side walls located 13.5 cm above the cage floor. The rats are tested in the presence of white noise (62 dB) and red light (60 watt).

Test compound is administered IV in a 50% PEG vehicle 5 minutes prior to the test session. A range of compound doses is typically used and 6 to 8 rats are tested at each dose. The animal's movement time, vertical activity, and total distance traveled are tracked over a 15 minute test session. A sedative, or hypnotic, effect in the spontaneous locomotor activity model is defined by a decrease in any two of these three measures relative to animals given vehicle alone.

c. Step-Down Passive Avoidance

In step-down passive avoidance a rat is placed on a platform located in the center of an electrified grid floor that is contained within a large (45 cm×45 cm×50 cm) white translucent Plexiglas enclosure. The natural inclination of the rat is to step off the platform and investigate its surroundings. In day one of the experiment animals are treated with either Zolpidem, test compound in a 50% PEG vehicle, or vehicle alone and then trained to remain on the platform for at least 120 seconds. Each time the animal steps off the platform it receives a mild foot shock of 2 mAmps×6 sec. Following each shock the animal is removed from the box, placed in its cage for a one minute inter-trial interval, and then returned to the platform. The latency to step down on each trial, the number of trials taken to reach criterion during training and the retention latency are collected.

Testing is conducted approximately 24 hrs. after training. Drug-free animals are placed on the platform in the box in which they will have been trained and the latency to step down onto the grid floor is recorded for one trial as a measure of memory retention. The animal is allowed a maximum of 120 seconds to step down and does not receive a shock upon stepping off the platform.

d. Porsolt Forced Swim Test

The effects measured in this model have been correlated to antidepressant efficacy for drugs. The paradigm of this model is that an effective antidepressant compound will cause a rat to make greater attempts to escape a water-filled cylinder than a rat given vehicle only.

Animals used in this study were non-naive male Sprague Dawley Rats (SASCO, St. Louis) weighing between 280–350 grams. The test apparatus consists of 6 clear Plexiglas® cylinders 40 cm high×19 cm wide. Cylinders are filled to 18 cm with 25° C. water. Each rat is placed in a cylinder for a 15 minute training session. Following either subchronic or acute dosing of either vehicle (0.5% methylcellulose) of compound, animals are brought back 24 hours later for a 5 minute test session. These test session is videotaped for later scoring.

Subchronic dosing consists of administering drug three times in the 24-hour period between training and testing. The drug is administered 24 hrs., 5 hrs., and 1 hr. prior to the test session. Acute dosing consists of administering the drug once, 1 hour prior to the test session. Scoring is done using a time-sampling computer program written in Visual Basic and run in DOS. Every five seconds, animals are rated as demonstrating one of three behaviors: immobility, mild swim, or climbing. These sampling score are then converted into percentages of the test session.

e. Spatial Water Maze

The spatial water maze has been used extensively as a test of spatial learning and memory. Rats are trained to escape from the water by swimming to a platform that is submerged just below the surface of the water. Since the platform is not visible to the animal, it has to utilize visual extra-maze cues in the area of the tank to locate the platform.

The water maze apparatus consists of a circular tank, 119 cm in diameter and 56 cm in height, with a black interior. The tank is filled with water approximately 23–25° C. to a height of 42 cm. Superimposed onto the tank are four quadrants, South, East, North and West. The tank is surrounded by external visual cues, which consist of a black and white checkered wall, a black and white striped wall, a white wall with two light fixtures, and a blue wall. A black circular PLEXIGLAS platform with a black neoprene rubber top is placed in the Northeast quadrant approximately 1–2 cm below the surface of the water. The submerged platform is 39 cm in height and has a diameter of 11.5 cm. Training and testing are conducted in the presence of a 60–62 dB white noise source and under dim light conditions (1.0–1.2 lux) The animal's path is tracked by a video camera interfaced to an automated tracking package (Videotrack, CPL Systems).

Acquisition Training: Training consists of six trials. Test compound is administered IV in a 50% PEG vehicle 5 minutes prior to the test session. A range of doses is typically used and 8 to 10 rats are tested at each dose. Each animal is placed on the platform in the tank for 20 seconds prior to the first trial of acquisition training. For the first trial, the animal is placed in the water facing the wall of the tank at the "South" starting position. The order of training trials is South, East, North, and West. Each of the training trials is separated by an inter-trial interval (ITI) of 3 minutes. Each trial ends with the animal finding the platform or being placed onto it after 90 sec. Rats are then given 10 seconds on the platform and removed from the maze for the ITI. Each trial ends with the animal finding the platform or being placed onto it after 90 seconds. Rats are then given 10 seconds on the platform and removed from the maze for the ITI. During the ITI, each rat is dried off with a towel and placed in a heating chamber maintained at 45° C. The latency to reach the submerged platform (measured in seconds), the total distance traveled in the maze (measured in meters), the number of zone or quadrant transitions made, and the swim speed (measured in meters/sec.) on each trial are all recorded. Upon completion of training animals are returned to their home cages in the vivarium.

Retention Testing: Approximately 24 hours after training each rat is tested for retention on one trial. The rat is placed the "South" starting position and given 90 seconds to located the platform. The latency to locate the platform, total distance traveled, number of zone transitions and swim speed are all recorded by computer.

f. Bicuculline Seizure Threshold Test:

This test provides a measure of whether the test compound is proconvulsant by measuring whether the test compound produces any change in the dose of the seizure inducing drug, bicuculline, needed to elicit seizures in rats.

Test compounds must show <25% decrease in seizure threshold or p>0.05 significance to be considered as drug candidates.

Adult male Sprague-Dawley rats (175–300 g) are weighed and placed in a rat restrainer. A Teflon® indwelling catheter is placed in one of the lateral tail veins and held in place with surgical tape. The catheter and a 3.0 cc syringe are connected by a length of PE-100 tubing fitted with Hamilton male and female adapter. Patency of catheter placement is tested by backflow of venous blood and ready infusion of less than 2 ml of saline solution. Animals are placed in a clear acrylic cage for behavioral observation.

The test compound is prepared in either 25% or 50% polyethylene glycol 400 (PEG) vehicle. A bicuculline (BIC) stock solution of 1.0 mg/ml BIC in 25% PEG/75% 1N HCl is also prepared. Immediately prior to infusion 0.5 ml of BIC stock is diluted to 20 ml with 19.5 ml of ice cold saline.

Test compound is infused 5 minutes prior to the start of bicuculline infusion. Injection volumes do not exceed 4.0 ml/kg and are typically 1.0 or 2.0 ml/kg. The catheter is flushed immediately with 2.0 ml of saline to ensure total delivery of the drug. The catheter is then preloaded with dilute pontamine skye blue dye followed by some air to allow observation of the initiation of the bicuculline infusion. The BIC solution is delivered at a speed of 2.0 ml/minute by a constant speed infusion pump. The final infusion rate of bicuculline is approximately 0.05 mg/minute. The time elapsed from the start of bicuculline infusion to first myoclonic jerk (first head/neck twitch), the initiation of full myoclonus (writhing), and final forelimb extension is all recorded using a digital stopwatch. Animals are subsequently euthanized. The bicuculline seizure threshold is defined as the amount of bicuculline required to titrate the first myoclonic jerk. Bicuculline seizure threshold is expressed in mg/kg as follows:

$$\frac{[\text{time of myoclonic jerk (minutes)}] \times [\text{infusion rate (mg/minute)}]}{[\text{weight of animal (kg)}]}$$

g. Pentelenetetrazol Seizure Threshold Test

This assay may be used as an alternative to the bicuculline seizure threshold test to determine whether a test compound is proconvulsant. Pentelenetetrazol (PTZ) is used to induce seizures rather than bicuculline. Compound is administered 5 minutes prior to infusion of PTZ as in the bicuculline seizure threshold test. PTZ (2.5 mg/ml in 0.09% NaCl) is infused at a constant rate of 1.92 ml/minute with a syringe pump or a constant drug delivery rate of 4.8 mg/minute. The time elapsed from the start of PTZ infusion to first myoclonic jerk (first head/neck twitch), the initiation of full myoclonus (writhing), and final forelimb extension is recorded using a digital stopwatch. The PTZ seizure threshold is defined as the amount of infused PTZ required to titrate the first myoclonic jerk and is calculated by the same relationship as used for the bicuculline seizure threshold. In either the bicuculline or the PTZ seizure threshold test compounds should decrease the seizure threshold by less than a 25% decrease or not show a significant effect at the p<0.05 level.

Example 4

Anxiolytic Compounds

The compounds listed in Table V were tested by each of the methods described above for identifying anxiolytics compounds and compared to the known anxiolytic Alprazolam. Alprazolam is known to cause side effects including sedation.

TABLE V

| | Ro15-1788 binding, | oocyte electrophysiology (EC$_{50}$ (nM)/ maximum potentiation (%)) | | | | In vivo Behavioral assays[†] | |
|---|---|---|---|---|---|---|---|
| compound | K$_i$ (nM) | $\alpha_1\beta_2\gamma_2$ | $\alpha_2\beta_3\gamma_2$ | $\alpha_3\beta_3\gamma_2$ | $\alpha_5\beta_3\gamma_2$ | elevated plus maze | spontaneous locomotor activity |
| Alprazolam | 3.3 | 37/327 | 12/333 | 69/774 | 10/206 | 0.0625 | 0.125 |
| compound 1 | 3.6 | 6/12 | 20/71 | 35/72 | 89/−11 | 0.03 | NS |
| compound 2 | 10 | 33/18 | 12/40 | 23/39 | 36/−11 | 0.5 | 4 |
| compound 3 | 4.7 | 107/26 | 108/52 | 133/68 | 186/38 | 0.125 | NS* |
| compound 4 | 14 | 48/23 | 19/66 | 51/48 | 0 | 0.5 | NS |
| compound 5 | 8.3 | 0 | 9/44 | 21/44 | 0 | 0.5 | NS |

[†]For behavioral assays results are given as the minimal efficacious dose of compound in mg/kg, administered IV, needed to elicit a statistically significant response.
*NS: no statistically significant effect was observed over the dose range studied.

The structures of the above compounds are given in Table VI

TABLE VI

| Compound Number | Structure |
|---|---|
| compound 1 | 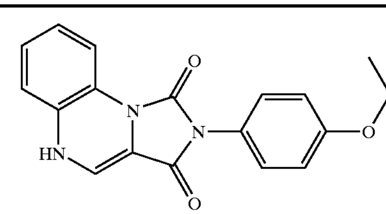 |
| compound 2 | 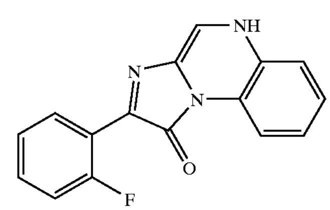 |

TABLE VI-continued

| Compound Number | Structure |
|---|---|
| compound 3 | 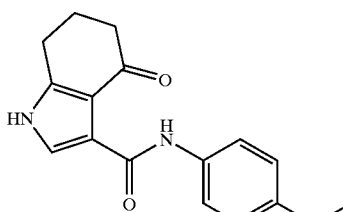 |
| compound 4 | 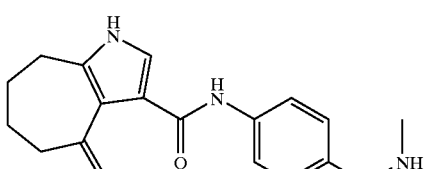 |
| compound 5 | 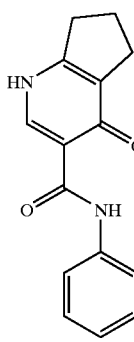 |

Example 5

Hypnotic Compounds

The compounds listed in Table VII were tested by the methods described above for identifying hypnotic compounds and compared to the known hypnotic Zolpidem. Zolpidem is known to display side effects including cognitive impairment.

The structures of Compounds 6–9 are shown in Table VIII.

TABLE VIII

| Compound Number | Structure |
|---|---|
| compound 6 | 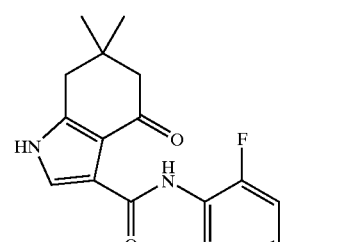 |
| compound 7 | 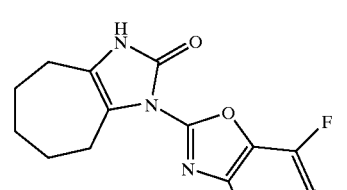 |
| compound 8 | 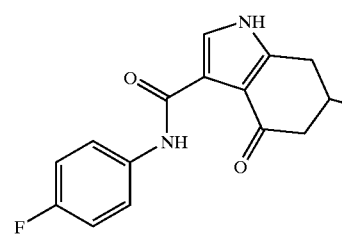 |
| compound 9 | 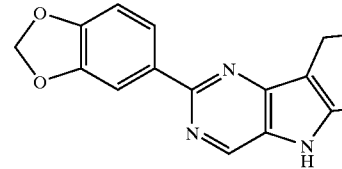 |

TABLE VII

| compound | Ro15-1788 binding, $K_i$ (nM) | oocyte electrophysiology ($EC_{50}$ (nM)/ maximum potentiation (%)) | | | | spontaneous locomotor activity* | step-down passive avoidance |
|---|---|---|---|---|---|---|---|
| | | $\alpha_1\beta_2\gamma_2$ | $\alpha_2\beta_3\gamma_2$ | $\alpha_3\beta_3\gamma_2$ | $\alpha_5\beta_3\gamma_2$ | | |
| Zolpidem | 48 | 178/263 | 553/350 | 1776/882 | >3 µM/<20 | 0.25 | 0.5 |
| compound 6 | 11 | 44/25 | 28/72 | 33/95 | 108/42 | 0.25 | 4 |
| compound 7 | 3 | 5/18 | 4/51 | 9/83 | 174/−23 | 0.125 | NS† |
| compound 8 | 24 | 14/17 | 39/42 | 37/61 | 40/16 | 0.5 | NS |
| compound 9 | 7.8 | 74/33 | 184/53 | 331/23 | ***/<10 | 0.5 | 0.5 |

*Minimal efficacious dose of compound, administered IV, needed to elicit a statistically significant response (mg/kg).
†NS indicates that no statistically significant effect was observed in this assay over the dose range studied.
***No meaningful value obtained.

Example 6

Antidepressant Compounds

The compounds shown in Table IX were tested by each of the methods described above and compared to the antidepressant compound Ro16–6028.

TABLE IX

| compound | Ro15-1788 binding, $K_i$ (nM) | oocyte electrophysiology ($EC_{50}$ (nM)/ maximum potentiation (%)) | | | | Porsolt swim test[†] | spontaneous locomotor activity |
|---|---|---|---|---|---|---|---|
| | | $\alpha_1\beta_2\gamma_2$ | $\alpha_2\beta_3\gamma_2$ | $\alpha_3\beta_3\gamma_2$ | $\alpha_5\beta_3\gamma_2$ | | |
| Ro16-6028 | 0.48 | 3/40 | 5/37 | 5/76 | 3/64 | 1 | 0.06 |
| compound 1 | 8 | 159/12 | 114/41 | 144/63 | 88/15 | 20 | NS* |
| compound 3 | 10 | 33/18 | 12/40 | 23/39 | 36/−11 | 20 | 4 |
| compound 4 | 4.7 | 107/26 | 108/52 | 133/68 | 186/38 | 20 | NS |

[†]Minimal efficacious dose of compound, administered IV, needed to elicit a statistically significant response (mg/kg).
*NS indicates that no statistically significant effect was observed in this assay over the dose range studied.
The compounds shown in Table IX also met the criteria for anxiolytic compounds. The structures for these compounds are given in Table VI, above.

Example 7

Cognition Enhancing Compounds

The following compounds were tested by the methods described above for identifying cognition enhancing compounds and compared to CGS 8216, a compound that has been shown to have a positive effect in models of learning and memory. We have also shown CGS 8216 to be efficacious in the step-down passive avoidance model (0.06 mg/kg minimal efficacious dose). Additionally it is know that CGS 8216 is anxiogenic and proconvulsant.

TABLE X

| compound | Ro15-1788 binding, $K_i$ (nM) | oocyte electrophysiology ($EC_{50}$ (nM)/ maximum potentiation (%)) | | | | cognitive model[†] | bicuculline seizure threshold[‡] |
|---|---|---|---|---|---|---|---|
| | | $\alpha_1\beta_2\gamma_2$ | $\alpha_2\beta_3\gamma_2$ | $\alpha_3\beta_3\gamma_2$ | $\alpha_5\beta_3\gamma_2$ | | |
| CGS 8216 | 0.2 nM | 0.7/−26 | 2/−10 | 2/−8 | 1/−39 | NS* | 50% |
| compound 10 | 10 | 0 | 31/22 | 46/23 | 81/−27 | 0.25 | NS |
| compound 11 | 33 | 21/−11 | 96/21 | 177/36 | 847/−22 | PO = 10.0[††] | NS |
| compound 12 | 5.4 | 18/15 | 11/63 | 18/82 | 19/−12 | 0.06 | NS |
| compound 13* | 6.3 | 3/−17 | 53/9 | 36/14 | 23/−20 | 0.125[††] | NS |

[†]The cognitive model is the step-down passive avoidance model. The result is given as the minimal efficacious dose of compound in mg/kg, administered IV.

[††]The cognitive model is the spatial water maze model. For the spatial water maze assay, results are given as the minimal efficacious dose of compound in mg/kg, administered IV (unless listed as PO), needed to elicit a statistically significant response.

[‡]Mean percent decrease in seizure threshold over the dose range studied.

*NS indicates that no statistically significant effect was observed in this assay in compound versus vehicle treated animals over the dose range studied.

Structures for Compounds 10–13 above are presented in Table XI.

TABLE XI

| Compound Number | Structure |
|---|---|
| compound 10 | (structure: benzimidazo-quinoxaline dione with 4-fluorophenyl) |
| compound 11 | (structure: 2-fluoro-methoxyphenyl tetrahydro-pyrimido-indole) |
| compound 12 | (structure: indole-carboxamide with hydroxyethoxy-phenyl and cyclohexanone fused) |
| compound 13** | (structure: cycloheptanone-fused pyrrole carboxamide with phenyl) |

The foregoing describes preferred embodiments of the present invention. Those of skill in the art will recognize that modifications may be made therein without departing from the spirit or scope of the present invention as set forth in the following claims, which conclude this specification.

What is claimed is:

1. A method for screening compounds for hypnotic activity, comprising:
    a) determining $EC_{50}$ and in vitro efficacy of each compound at an $\alpha_2\beta_3\gamma_2$ $GABA_A$ subtype receptor or an $\alpha_3\beta_3\gamma_2$ $GABA_A$ subtype receptor;
    b) determining in vitro efficacy of each compound at a $GABA_A$ receptor comprised of an $\alpha_1$ or $\alpha_5$ subunit; and
    c) selecting a compound having an $EC_{50}$ determined in a) of less than 200 nM, an in vitro efficacy determined in a) of greater than 10% for said $\alpha_2\beta_3\gamma_2$ $GABA_A$ subtype receptor or greater than 50% for said $\alpha_3\beta_3\gamma_2$ $GABA_A$ subtype receptor; and an in vitro efficacy value determined in b) of less than 50% for the $GABA_A$ receptor comprised of an $\alpha_1$ subunit or less than 45% for the $GABA_A$ receptor comprised of an $\alpha_5$ subunit.

2. The method of claim 1 wherein the in vitro efficacy value measured at said $\alpha_2\beta_3\gamma_2$ receptor is greater than 20% or the in vitro efficacy value measured said $\alpha_3\beta_3\gamma_2$ $GABA_A$ receptor is greater than 60%.

3. The method of claim 2 wherein the in vitro efficacy value measured at the $GABA_A$ receptor comprised of said $\alpha_1$ subunit is less than 45% or the in vitro efficacy value measured at the $GABA_A$ receptor comprised of said $\alpha_5$ subunit is less than 40%.

4. The method of claim 1 wherein the in vitro efficacy value measured at the $GABA_A$ receptor comprised of said $\alpha_1$ subunit is less than 45% or the in vitro efficacy value measured at the $GABA_A$ receptor comprised of said $\alpha_5$ subunit is less than 40%.

5. The method of claim 1 wherein the $EC_{50}$ measured at said $\alpha_2\beta_3\gamma_2$ $GABA_A$ subtype receptor or at said $\alpha_3\beta_3\gamma_2$ $GABA_A$ subtype receptor is less than 150 nM.

6. The method of claim 5 wherein the in vitro efficacy measured at said $\alpha_2\beta_3\gamma_2$ $GABA_A$ subtype receptor is greater than 20% or the in vitro efficacy measured said $\alpha_3\beta_3\gamma_2$ $GABA_A$ subtype receptor is greater than 60%.

7. The method of claim 6 wherein the in vitro efficacy measured at the $GABA_A$ receptor comprised of said $\alpha_1$ subunit is less than 45% or the in vitro efficacy measured at the $GABA_A$ receptor comprised of said $\alpha_5$ subunit is less than 40%.

8. The method of claim 5 wherein the in vitro efficacy measured at the $GABA_A$ receptor comprised of said $\alpha_1$ subunit is less than 45% or the in vitro efficacy measured at the $GABA_A$ receptor comprised of said $\alpha_5$ subunit is less than 40%.

9. The method of claim 1 wherein the $GABA_A$ receptor comprised of an $\alpha_1$ subunit is an $\alpha_1\beta_2\gamma_2$ $GABA_A$ subtype receptor or the $GABA_A$ receptor comprised of an $\alpha_5$ subunit is an $\alpha_5\beta_3\gamma_2$ $GABA_A$ subtype receptor.

10. A method for screening a plurality of compounds so as to identify at least one compound exhibiting hypnotic activity, comprising:
    a) selecting a plurality of compounds having a binding affinity of less than 100 nM at any $GABA_A$ receptor.
    b) determining $EC_{50}$ and in vitro efficacy values for each selected compound at an $\alpha_2\beta_3\gamma_2$ $GABA_A$ subtype receptor or at an $\alpha_3\beta_3\gamma_2$ $GABA_A$ subtype receptor;
    c) determining in vitro efficacy values for each selected compound at a $GABA_A$ receptor comprised of an $\alpha_1$ or an $\alpha_5$ subunit; and
    d) identifying as exhibiting hypnotic activity each selected compound having an $EC_{50}$ value determined in b) of less than 200 nM, an in vitro efficacy value measured in b) of greater than 10% for said $\alpha_2\beta_3\gamma_2$ $GABA_A$ subtype receptor or greater than 50% for said $\alpha_3\beta_3\gamma_2$ $GABA_A$ subtype receptor, and an in vitro efficacy value determined in c) of less than 50% for the $GABA_A$ receptor comprised of said $\alpha_1$ subunit or less than 45% for the $GABA_A$ receptor comprised of said $\alpha_5$ subunit.

11. A method for screening a plurality of compounds so as to identify compounds exhibiting hypnotic activity, comprising:
    a) measuring the $EC_{50}$ and in vitro efficacy of each compound at an $\alpha_2\beta_3\gamma_2$ $GABA_A$ subtype receptor or an $\alpha_3\beta_3\gamma_2$ $GABA_A$ subtype receptor;
    b) measuring the in vitro efficacy of each compound at a $GABA_A$ receptor comprised of an $\alpha_1$ or $\alpha_5$ subunit; and
    c) measuring the in vivo effect of each compound in an animal model indicative of hypnotic effects;
    d) measuring the in vivo effect of each compound in an animal model indicative of cognitive impairment; and
    e) identifying a compound as having hypnotic activity when the $EC_{50}$ measured in step a) is less than 200 nM, the in vitro efficacy measured in step a) is greater than 10% for said $\alpha_2\beta_3\gamma_2$ $GABA_A$ subtype receptor or greater than 50% for said $\alpha_3\beta_3\gamma_2$ GABA$_A$ subtype receptor, and the in vitro efficacy measured in step b) is less than 50% for the GABA$_A$ receptor comprised of said $\alpha_1$ subunit or less than 45% for the GABA$_A$ receptor comprised of said $\alpha_5$ subunit and said compound produces a statistically significant (p<0.05) positive effect in the animal model indicative of sedation and said compound does not produce a statistically significant effect in the animal model indicative of cognitive impairment.

12. A method for screening a plurality of compounds so as to identify at least one compound exhibiting hypnotic activity, comprising:

a) selecting compounds having a binding affinity less than 100 nM at any GABA$_A$ receptor;

b) measuring the EC$_{50}$ and in vitro efficacy of each selected compound at an $\alpha_2\beta_3\gamma_2$ GABA$_A$ subtype receptor or an $\alpha_3\beta_3\gamma_2$ GABA$_A$ subtype receptor;

c) measuring the in vitro efficacy of each selected compound at a GABA$_A$ receptor comprised of an $\alpha_1$ or $\alpha_5$ subunit; and d) measuring the in vivo effect of each selected compound in an animal model indicative of sedative effects;

e) measuring the in vivo effect of each selected compound in an animal model indicative of cognitive impairment; and f) identifying as having hypnotic activity each selected compound for which the EC$_{50}$ measured in step b) is less than 200 nM, the in vitro efficacy measured in step b) is greater than 10% for said $\alpha_2\beta_3\gamma_2$ GABA$_A$ subtype receptor or greater than 50% for said $\alpha_3\beta_3\gamma_2$ GABA$_A$ subtype receptor, and the in vitro efficacy measured in step c) is less than 50% for the GABA$_A$ receptor comprised of said $\alpha_1$ subunit or less than 45% for the GABA$_A$ receptor comprised of said $\alpha_5$ subunit and said compound produces a statistically significant (p<0.05) positive effect in the animal model indicative of hypnotic effects and said compound does not produce a statistically significant effect in the animal model indicative of cognitive impairment.

* * * * *